(12) United States Patent
Serlie et al.

(10) Patent No.: US 12,182,082 B2
(45) Date of Patent: Dec. 31, 2024

(54) DATA REPOSITORIES

(71) Applicant: KONINKLIJKE PHILIPS N.V., Eindhoven (NL)

(72) Inventors: Iwo Willem Oscar Serlie, Best (NL); Josephus Antonius Maria Schipperheijn, Eindhoven (NL); Roy Franciscus Petrus Van Pelt, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 322 days.

(21) Appl. No.: 16/630,971

(22) PCT Filed: Jul. 12, 2018

(86) PCT No.: PCT/EP2018/068893
§ 371 (c)(1),
(2) Date: Jan. 14, 2020

(87) PCT Pub. No.: WO2019/016059
PCT Pub. Date: Jan. 24, 2019

(65) Prior Publication Data
US 2020/0226106 A1    Jul. 16, 2020

(30) Foreign Application Priority Data
Jul. 18, 2017   (NL) .................. 17181909.7

(51) Int. Cl.
*G06F 16/21* (2019.01)
*G16H 10/60* (2018.01)
*G16H 40/20* (2018.01)

(52) U.S. Cl.
CPC .......... *G06F 16/212* (2019.01); *G16H 10/60* (2018.01); *G16H 40/20* (2018.01)

(58) Field of Classification Search
CPC ...... G06F 16/212; G16H 40/20; G16H 10/60; G16H 30/20
See application file for complete search history.

(56) References Cited

U.S. PATENT DOCUMENTS

| | | | |
|---|---|---|---|
| 5,553,216 | A | 9/1996 | Yoshioka et al. |
| 8,392,464 | B2 | 3/2013 | Bloesch et al. |
| 2003/0028401 | A1 | 2/2003 | Kaufman et al. |
| 2005/0223325 | A1 | 10/2005 | Naitou |
| 2010/0257190 | A1* | 10/2010 | Farkash ............... G16H 30/20 707/760 |

(Continued)

OTHER PUBLICATIONS

International Search Report and Written Opinion, International Application No. PCT/EP2018/068893, Mailed on Oct. 11, 2018.

(Continued)

*Primary Examiner* — Hosain T Alam
*Assistant Examiner* — Chongsuh Park

(57) ABSTRACT

Presented are concepts for provisioning an instance of a data repository. A domain model specification is obtained, the domain model specification comprising: an entity definition defining an entity of a data repository to be provisioned; and an operation definition defining one or more operations to be supported by the data repository to be provisioned. An instance of a data repository is generated based on the entity definition and operation definition of the domain model specification.

15 Claims, 3 Drawing Sheets

(56) References Cited

U.S. PATENT DOCUMENTS

2013/0238351 A1* 9/2013 Burns .................... G16H 10/20
705/2

OTHER PUBLICATIONS

"Database", Wikipedia, Accessed Sep. 26, 2018.
"Open Source FHIR implementations", https://wiki.hl7.org/index. php?title=Open_Source_FHIR_implementations, Accessed Jan. 10, 2020.
Fridsma, D. et al., "The BRIDG Project: A Technical Report", J Am Med Inform Assoc., 2008, pp. 130-137.

* cited by examiner

DATA REPOSITORIES

This application is the U.S. National Phase application under 35 U.S.C. § 371 of International Application No. PCT/EP2018/068893, filed on 12 Jul. 2018, which claims the benefit of European Application Serial No. 17181909.7, filed 18 Jul. 2017. These applications are hereby incorporated by reference herein.

FIELD OF THE INVENTION

This invention relates to data repositories, and in particular to provisioning data repository instances.

BACKGROUND OF THE INVENTION

The use of computers and data repositories to store information, such as clinical data relating to one or more patients, is well known. A Clinical Data Repository (CDR) is data repository, or database, that is adapted to store the clinical information relating to patients, and typical types of patient data in a CDR include: laboratory test results; patient details; images (such as X-ray and radiological images); treatments; and treatment observations.

Various factors, such as technical competence, available resources, legal requirements or regulations, global knowledge, clinical guidelines, etc. mean that CDRs typically vary across implementations (so as to adhere to such factors). Accordingly, accessing CDRs, retrieving data from CDRs, and/or exchanging information from CDRs can be difficult or problematic due to a lack of implementation consistency.

In an attempt to address the issue of interoperability between CDR implementations, a standard known as HL7 Fast Health Interoperability Resources (FHIR) has been designed for enabling the electronic exchange/communication of healthcare-related information. The HL7 FHIR standard specifies base resources for different types of clinical and administrative information and, at present, there are Structured Query Language (SQL) and non-SQL (NoSQL) solutions which are not suitable for healthcare applications due to lacking scalability, query performance and maintenance.

Thus, there exists a need for CDR implementations that are flexible (e.g. allow customization to meet local variations in technical competence, resources, legal requirements, etc.) and simple to implement and maintain.

SUMMARY OF THE INVENTION

Some embodiments of the invention aims to at least partly fulfill one of the aforementioned needs. To this end, some embodiments of the invention provide devices, methods, computer program products and systems as defined in the independent claims. The dependent claims provide some advantageous embodiments.

According to example aspects, the invention provides an apparatus and a corresponding method for provisioning an instance of a data repository. The apparatus comprises: a data acquisition unit adapted to obtain a domain model specification, the domain model specification comprising: an entity definition defining an entity of a data repository to be provisioned; and an operation definition defining one or more operations to be supported by the data repository to be provisioned; and a processing unit adapted to generate an instance of a data repository based on the entity definition and operation definition of the domain model specification. The generated instance of a data repository comprises: an entity having one or more attributes defined by the entity definition; and a service interface adapted to support an operation defined by the operation definition.

Some embodiments may therefore automatically compose a hybrid repository instance based on an entity definition and an operations definition. By way of example, such a generated repository instance may comprise a normalized part that is optimized according to the operations definition. The generated repository instance may also comprise a entity-based (e.g. document-based) part according to the entity definition.

Some embodiments may be based on the concept of automatically generating an instance of a data repository based on a structured description of a domain model. By taking account of information relating to requirements of entities and operations for the data repository, a generated instance of a data repository may be customised according to the requirements. In this way, local variations may be accounted for without detailed and/or complex database engineering efforts. Thus, unlike classic table-based implementations via normalised database models, some embodiments may be simple and flexible to implement, deploy and maintain.

There may be provided a concept of implementing a specification-driven data repository instance. Such data repository instances may be particularly advantageous for storing clinical data (for which factors such as technical competence, available resources, legal requirements or regulations, global knowledge, clinical guidelines, etc. can vary widely depending on implementation). Automatic and flexible provisioning of Clinical Data Repositories (CDRs) may thus be provided by proposed embodiments.

For example, some embodiments may enable the automatic generation of a SQL-based CDR instance according to a structured definition of entities of a domain. Such a CDR instance may provide a fully-functional technical component that is configured to store, search and retrieve clinical information via an interface (e.g. web service). In this way, there may be provided a component that automatically implements a CDR service.

Exemplary embodiments may thus provide various technical effects such as:
reduced deployment risk in case of localization of data repositories;
fast response to updates of a standard with minimal software engineering effort;
fewer programming errors (as a result of increased automation);
efficient implementation of application-specific data repositories;
database maintenance may be transferred to the client-side, allowing for cloud based solutions;
continuous integration ("live updates") support may be provided; and
efficient retrieval of data, via automatic normalization of base models into tables.

Some embodiments may be of particular benefit to implementing or provisioning data repositories across various domains, wherein various domain-specific requirements may be prescribed. For this reason, some embodiments may be particularly useful for providing data repositories for clinical data, and examples are therefore described in the context of providing CDRs so as to provide an understanding of the proposed concept(s). However, it will be appreciated that the proposed concept(s) may be equally applicable outside the domain of clinical data, such as the field of administrative systems or content storage systems where scalable and searchable content is required for example.

By way of example, the domain model specification may comprise an operation definition which defines searching parameters of a search operation. The service interface may then be adapted to implement a search operation based on one or more searching parameters defined by the operation definition. In this way, embodiments may provide a hybrid data repository system that automatically optimises a search function in view of a domain model specification. The search function may be provisioned via an interface, thereby enabling retrievable, versioned content.

Some embodiments may enable real-time analytics without requiring a generic data warehouse. For example, the searching parameters may be adapted to relate to a plurality of resources so as to support a composite search query. Composite search queries combining multiple resources may therefore be included in the search parameter specification of search operation to dynamically optimize CDR performance for real-time specific 'in workflow' analytics depending on a local workflow. This may enable analytical and statistical data to be collected on input (when data is added to the CDR) to serve the analytics rather than being computed on demand. By way of further example, the domain model specification may comprise a structured description of one or more entities according to a predetermined specification format. Thus, a standardised form of domain description may be implemented, thereby simplifying the definition and/or provision of requirements prescribed by a domain. Reduced effort and/or understanding may therefore be required in order to provide and/or update a domain model specification, For the purpose of defining entity requirements of a domain in a simple and/or standardised manner, the domain model specification may in some embodiments comprise a structured description of the entity according to a predetermined specification format. In other embodiments, the entity definition of the domain model specification may comprise a definition of: an attribute of the entity; and permissible values of the attribute. Such embodiments may therefore leverage information about the attributes of an entity and the values these attributes are permitted have.

In some embodiments, the processing unit may be adapted to generate an SQL-server instance of the data repository based on the domain model specification. Automatic data search optimization may therefore be provided via SQL server normalization of searchable entities (e.g. content).

By way of example, the generated instance of the data repository may comprise: entity, junction and version tables; and searchable content and indices. This may provide the benefit that the repository design is specifically optimized so that domain model changes have minimal impact on the repository structure. This potentially allows an end-user to change the domain model specification through the web API on a live system. For example, adding an attribute to an entity requires no structural changes to the repository.

The data acquisition unit may be adapted to obtain an updated version of the domain model specification. The processing unit may then be adapted to modify the generated instance of a data repository based on the updated version of the domain model specification, thus creating an updated/modified instance. This provides the benefit that a user can deploy a new version of the repository at any time, instantaneously, by provisioning a new version of the domain model specification. Some embodiments may therefore enable the automatic updating of a data repository instance when a new version of a domain model specification is obtained. Minimal efforts may thus be required to update to a data repository.

The data repository may comprise a clinical data repository adapted to store clinical data relating to one or more patients. Such embodiments may therefore enable the provision of CDRs that are tailored according to local variations in requirements.

The data acquisition unit may comprise: an input interface adapted to receive an input signal representative of at least one of: the entity definition; and the operation definition; and a specification unit adapted to generate the domain model specification based on the received input signal. Such embodiments may cater for the provision of user-specified information which enables unique traits, entities, operation, circumstances and/or conditions specific to a domain or environment to be accounted for when provisioning a data repository instance. Thus, there may be provided a tool which enables a user to further specify factors to be included in the generation of a data repository instance, e.g. by specifying an entity or operation. Embodiments may therefore provide input options, increasing the flexibility and power of data repository provision.

In some embodiments, the apparatus may further comprise a communication interface adapted to communicate with one or more databases so as to obtain at least one of: the entity definition; and the operation definition.

Proposed embodiments may support dynamic data repository definition or generation according to a specific domain, context or situation.

According to another aspect, there may be provided data storage system comprising: a database adapted to store a plurality of data records; and apparatus for provisioning an instance of a data repository according to proposed embodiment. Also, in some embodiments, the plurality of data records may comprise one or more documents represented using a markup language (e.g. eXtensible Markup Laguage (XML) or JavaScript Object Notation (JSON)) and adapted to store data associated with an instance of a data repository generated by the processing unit.

The system may further comprise a display device for displaying a graphical or non-graphical (e.g. auditory) user interface, wherein the graphical user interface is adapted to communicate information about a provisioned data repository instance to a user.

Some embodiments may comprise a client device comprising a data processor device. This may be a standalone device adapted to receive information from one or more remotely positioned information sources (via a communication link for example) and/or even adapted to access information stored in a database for example. In other words, a user (such as a professional, technician, researcher, patient etc.) may have an appropriately arranged client device (such as a laptop, tablet computer, mobile phone, PDA, etc.) which provides a system according to an embodiment.

The system may comprise: a server device comprising at least one processor, where the server device may be configured to transmit generated instructions for provisioning a data repository instance to a client device or communication network. In such a configuration, display instructions are made available by a server. A user may therefore link with the server to work with the system.

The processor may be remotely located from the display device, and a control signal may thus be communicated to the display device via a communication link. Such a communication link can be e.g. the internet and/or a wireless communication link. Other suitable short-range or longrange communication links and/or protocols may be employed. In this way, a user (such as a researcher, technician, developer, patient etc.) may have an appropriately arranged device that can receive and process information according to an embodiment. Some embodiments may therefore enable a user to remotely manage and/or access data using a portable computing device, such as a laptop, tablet computer, mobile phone, PDA, etc. Some embodiments may also enable data retrieval.

The system may further comprise: a server device comprising at least one processor; and a client device comprising a display device. Dedicated data processing means may therefore be employed for the purpose of provisioning a data repository instance, thus reducing processing requirements or capabilities of other components or devices of the system.

Thus, it will be understood that processing capabilities may therefore be distributed throughout the system in different ways according to predetermined constraints and/or availability of processing resources.

According to another aspect of the invention, there may be provided a method for provisioning an instance of a data repository, the method comprising: obtaining a domain model specification comprising: an entity definition defining an entity of a data repository to be provisioned; and an operation definition defining one or more operations to be supported by the data repository to be provisioned; and generating an instance of a data repository based on the entity definition and operation definition of the domain model specification, wherein the generated instance of a data repository comprises: an entity having one or more attributes defined by the entity definition; and a service interface adapted to support an operation defined by the operation definition.

Some embodiments may further comprise obtaining an updated version of the domain model specification, and modifying the generated instance of a data repository based on the updated version of the domain model specification.

According to another aspect, there may be provided a computer program product downloadable from a communications network and/or stored on a computer readable medium and/or microprocessor-executable medium wherein the computer program product comprises computer program code instructions, which when executed by at least one processor, implement a method according to a proposed embodiment.

These and other aspects of the invention will be apparent from and elucidated with reference to the embodiment(s) described hereinafter.

BRIEF DESCRIPTION OF THE DRAWINGS

Embodiments of the invention will now be described in detail with reference to the following schematic drawings.

DETAILED DESCRIPTION OF THE EMBODIMENTS

Proposed is a concept for enabling the automatic provision of a data repository instance which takes account of a structured description of a domain model. In particular, the domain model may comprise information relating to requirements of entities and operations for the data repository. For instance, a generated repository instance may comprise: (i) a normalized part that is optimized according to an operations definition; and (ii) an entity-based according to a definition of one or more entities.

By taking account of requirements of entities and operations for a data repository, a generated instance of the data repository may be customised without detailed and/or complex database engineering efforts. Thus, unlike classic table-based implementations via normalised database models, proposed embodiments may be simple and flexible to implement, deploy and maintain.

Proposed embodiments may be particularly advantageous for storing clinical data (for which requirements or constraint can vary widely depending on implementation). For example, embodiments may enable the automatic generation of a SQL-based CDR instance according to a structured definition of entities of a clinical domain. The CDR instance may be configured to store, search and retrieve clinical information via an interface (e.g. web service). Dynamic and/or automatic provisioning of CDRs may thus be provided by proposed embodiments. However, it will be appreciated that the proposed concept(s) may be equally applicable outside the domain of clinical information, such as the field of administrative systems or content storage systems where scalable and searchable content is required for example.

Some embodiments are based on the insight that a hybrid repository instance may be automatically composed based on a structure definition and an operations definition. By adapting a repository instance to have a normalized part that is optimized according to the operations definition and an entity-based part according to the structure definition, there may be provided an optimized data representation which can be automatically adapted to operation parameters and structure definitions. Some embodiments may therefore be thought of as accounting for definitions of entities of a domain model and definitions of operations to generate a repository instance that is optimized to the specific constraints resulting from the entities and operations.

In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

Figure 1:
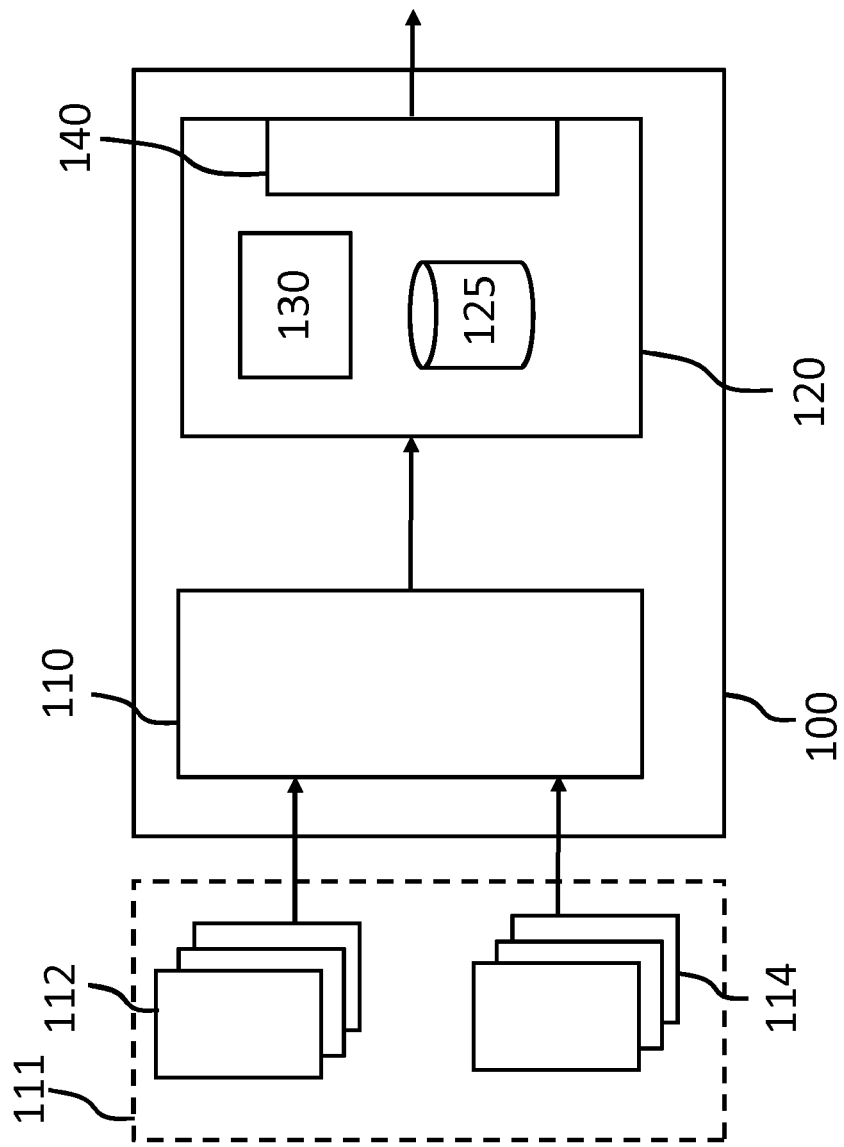
FIG. 1 is a simplified block diagram of an apparatus for provisioning an instance of a data repository according to an embodiment.

Referring to FIG. 1, there is depicted a simplified block diagram of an apparatus 100 for provisioning an instance of a data repository according to a proposed embodiment. The apparatus comprises a data acquisition unit 110 adapted to obtain a domain model specification 111.

In particular, the domain model specification 111 comprises entity definitions 112 defining entities of a data repository to be provisioned. The domain model specification 111 also comprises operation definitions 114 defining operations to be supported by the data repository to be provisioned The entity definitions 112 comprise structured descriptions of entities according to a predetermined specification format. For instance, an entity definition 112 of this example comprises a definition of: an attribute of the entity; and permissible values of the attribute. For this purpose, an entity description 112 may therefore be provided in accordance with the HL7 FHIR standard so as to facilitate the definition of an entity.

The operation definitions 114 comprises descriptions of operations that are to be catered for. For instance, an operation definition 114 of this example may comprise a definition of a searching operation, including searching parameters supported by the operation and permissible parameter values and/or formats. Again, for this purpose, an operation definition 114 may be provided in accordance with the HL7 FHIR standard so as to facilitate the definition of searching functionality for example.

The apparatus 100 also comprises a processing unit 120 adapted to generate an instance of a data repository based on the obtained entity definitions 112 and operation definitions 114 of the domain model specification 111. More specifically, in the example of FIG. 1, the processing unit 120 is adapted to generate an instance of a data repository comprising: (i) entities 125 having attributes defined by the entity definitions 112; and (ii) a service module 130 adapted to support operations defined by the operation definitions 114. For example, where an operation definition 114 defines searching parameters of a searching operation, the service module 130 is adapted to implement a search operation based on the searching parameter(s) defined by the operation definition 114.

One or more results of operations facilitated by the service module 130 can be output to a user or entity via an output interface 140 of the processing unit 120.

By way of facilitating an improved understanding of proposed embodiments, an example of an entity definition and an operation definition that may be employed will now be provided.

More specifically, an example of a structured definition for a domain model entity called "Person" according to the HL7 healthcare interoperability standard FHIR is as follows:

```xml
<?xml version="1.0" encoding="UTF-8"?>
<StructureDefinition xmlns="http://hl7.org/fhir">
  <id value="Person"/>
  <meta>
    <lastUpdated value="2015-09-30T23:39:40.637+10:00"/>
  </meta>
  <text>
    <status value="generated"/>
    <div xmlns="http://www.w3.org/1999/xhtml">
      Narrative describing the entity.
    </div>
  </text>
  <url value="http://hl7.org/fhir/StructureDefinition/Person"/>
  <name value="Person"/>
  <status value="draft"/>
  <publisher value="Health Level Seven International (Patient Administration)"/>
  <contact>
    <telecom>
      <system value="other"/>
      <value value="http://hl7.org/fhir"/>
    </telecom>
  </contact>
  <date value="2015-09-30T23:39:40+10:00"/>
  <description value="Base StructureDefinition for Person Resource"/>
  <requirements value="Need to track persons potentially across multiple roles."/>
  <fhirVersion value="1.0.1"/>
  <kind value="resource"/>
  <abstract value="false"/>
  <base value="http://hl7.org/fhir/StructureDefinition/DomainResource"/>
  <snapshot>
    <element>
      <path value="Person"/>
      <short value="A generic person record"/>
      <definition value="Demographics and administrative information about a person independent of a specific health-related context."/>
      <min value="0"/>
      <max value="*"/>
      <type>
        <code value="DomainResource"/>
      </type>
      <mapping>
        <identity value="w5"/>
        <map value="administrative.entity"/>
      </mapping>
    </element>
    <element>
      <path value="Person.id"/>
      <short value="Logical id of this artifact"/>
      <definition value="The logical id of the resource, as used in the URL for the resource. Once assigned, this value never changes."/>
      <min value="0"/>
      <max value="1"/>
      <type>
        <code value="id"/>
      </type>
```

```
        </element>
        <element>
           <path value="Person.meta"/>
           <short value="Metadata about the resource"/>
           <definition value="The metadata about the resource. This is content that is
maintained by the infrastructure. Changes to the content may not always be associated with
version changes to the resource."/>
           <min value="0"/>
           <max value="1"/>
           <type>
              <code value="Meta"/>
           </type>
        </element>
        <element>
           <path value="Person.text"/>
           <short value="Text summary of the resource, for human interpretation"/>
           <definition value="A human-readable narrative that contains a summary of the
resource, and may be used to represent the content of the resource to a human. The narrative
need not encode all the structured data, but is required to contain sufficient detail to make it
"clinically safe" for a human to just read the narrative. Resource definitions may
define what content should be represented in the narrative to ensure clinical safety."/>
           <alias value="narrative"/>
           <alias value="html"/>
           <alias value="xhtml"/>
           <alias value="display"/>
           <min value="0"/>
           <max value="1"/>
           <type>
              <code value="Narrative"/>
           </type>
           <condition value="dom-1"/>
        </element>
        <element>
           <path value="Person.extension"/>
           <short value="Additional Content defined by implementations"/>
           <definition value="May be used to represent additional information that is not part of
the basic definition of the resource. In order to make the use of extensions safe and
manageable, there is a strict set of governance applied to the definition and use of extensions.
Though any implementer is allowed to define an extension, there is a set of requirements that
SHALL be met as part of the definition of the extension."/>
           <alias value="extensions"/>
           <alias value="user content"/>
           <min value="0"/>
           <max value="*"/>
           <type>
              <code value="Extension"/>
           </type>
        </element>
        <element>
           <path value="Person.identifier"/>
           <short value="A human identifier for this person"/>
           <definition value="Identifier for a person within a particular scope."/>
           <requirements value="People are known by a variety of ids. Some institutions
maintain several, and most collect identifiers for exchange with other organizations
concerning the person. Examples are national person identifier and local identifier."/>
           <min value="0"/>
           <max value="*"/>
           <type>
              <code value="Identifier"/>
           </type>
        </element>
        <element>
           <path value="Person.name"/>
           <short value="A name associated with the person"/>
           <definition value="A name associated with the person."/>
           <requirements value="Need to be able to track the person by multiple names.
Examples are your official name and a partner name."/>
           <min value="0"/>
           <max value="*"/>
           <type>
              <code value="HumanName"/>
           </type>
```

-continued

```
      </element>
      <element>
        <path value="Person.telecom"/>
        <short value="A contact detail for the person"/>
        <definition value="A contact detail for the person, e.g. a telephone number or an
email address."/>
        <requirements value="People have (primary) ways to contact them in some way such
as phone, email."/>
        <min value="0"/>
        <max value="*"/>
        <type>
          <code value="ContactPoint"/>
        </type>
      </element>
      <element>
        <path value="Person.gender"/>
        <short value="male | female | other | unknown"/>
        <definition value="Administrative Gender."/>
        <requirements value="Needed for identification of the person, in combination with (at
least) name and birth date. Gender of person drives many clinical processes."/>
        <min value="0"/>
        <max value="1"/>
        <type>
        <code value="code"/>
        </type>
        <binding>
          <strength value="required"/>
          <description value="The gender of a person used for administrative purposes."/>
          <valueSetReference>
            <reference value="http://hl7.org/fhir/ValueSet/administrative-gender"/>
          </valueSetReference>
        </binding>
      </element>
      <element>
        <path value="Person.birthDate"/>
        <short value="The date on which the person was born"/>
        <definition value="The birth date for the person."/>
        <requirements value="Age of person drives many clinical processes, and is often used
in performing identification of the person. Times are not included so as to not confuse things
with potential timezone issues."/>
        <min value="0"/>
        <max value="1"/>
        <type>
          <code value="date"/>
        </type>
      </element>
      <element>
        <path value="Person.address"/>
        <short value="One or more addresses for the person"/>
        <definition value="One or more addresses for the person."/>
        <requirements value="May need to keep track of person's addresses for
contacting, billing or reporting requirements and also to help with identification."/>
        <min value="0"/>
        <max value="*"/>
        <type>
          <code value="Address"/>
        </type>
      </element>
      <element>
        <path value="Person.photo"/>
        <short value="Image of the person"/>
        <definition value="An image that can be displayed as a thumbnail of the person to
enhance the identification of the individual."/>
        <min value="0"/>
        <max value="1"/>
        <type>
          <code value="Attachment"/>
        </type>
      </element>
      <element>
        <path value="Person.managingOrganization"/>
        <short value="The organization that is the custodian of the person record"/>
        <definition value="The organization that is the custodian of the person record."/>
        <requirements value="Need to know who recognizes this person record, manages and
updates it."/>
```

```
            <min value="0"/>
            <max value="1"/>
            <type>
               <code value="Reference"/>
               <profile value="http://hl7.org/fhir/StructureDefinition/Organization"/>
            </type>
         </element>
         <element>
            <path value="Person.active"/>
            <short value="This person's record is in active use"/>
            <definition value="Whether this person's record is in active use."/>
            <requirements value="Need to be able to mark a person record as not to be used
because it was created in error."/>
            <min value="0"/>
            <max value="1"/>
            <type>
               <code value="boolean"/>
            </type>
            <isModifier value="true"/>
         </element>
      </snapshot>
</StructureDefinition>
```

Next, an example of search parameter definitions for a domain model entity according to the HL7 healthcare interoperability standard FHIR is as follows:

```
<?xml version="1.0" encoding="utf-8"?>
<Bundle xmlns="http://hl7.org/fhir">
   <id value="searchParams" />
   <type value="collection" />
   <entry>
      <fullUrl value="http://hl7.org/fhir/SearchParameter/DomainResource-text" />
      <resource>
         <SearchParameter>
            <id value="Person-identifier" />
            <url value="http://hl7.org/fhir/SearchParameter/Person-identifier" />
            <name value="identifier" />
            <status value="draft" />
            <experimental value="false" />
            <publisher value="Health Level Seven International (Patient Administration)" />
            <contact>
               <telecom>
                  <system value="url" />
                  <value value="http://hl7.org/fhir" />
               </telecom>
            </contact>
            <contact>
               <telecom>
                  <system value="url" />
                  <value value="http://www.hl7.org/Special/committees/pafm/index.cfm" />
               </telecom>
            </contact>
            <code value="identifier" />
            <base value="Person" />
            <type value="token" />
            <description value="A person Identifier" />
            <expression value="Person.identifier" />
            <xpath value="f:Person/fidentifier" />
            <xpathUsage value="normal" />
         </SearchParameter>
      </resource>
   </entry>
   <entry>
      <fullUrl value="http://hl7.org/fhir/SearchParameter/Person-link" />
      <resource>
         <SearchParameter>
            <id value="Person-link" />
            <url value="http://hl7.org/fhir/SearchParameter/Person-link" />
            <name value="link" />
            <status value="draft" />
            <experimental value="false" />
            <publisher value="Health Level Seven International (Patient Administration)" />
            <contact>
               <telecom>
                  <system value="url" />
```

-continued

```
              <value value="http://hl7.org/fhir" />
            </telecom>
          </contact>
          <contact>
            <telecom>
              <system value="url" />
              <value value="http://www.hl7.org/Special/committees/pafm/index.cfm" />
            </telecom>
          </contact>
          <code value="link" />
          <base value="Person" />
          <type value="reference" />
          <description value="Any link has this Patient, Person, RelatedPerson or
Practitioner reference" />
          <expression value="Personlink.target" />
          <xpath value="f:Person/f:link/f:target" />
          <xpathUsage value="normal" />
          <target value="Practitioner" />
          <target value="Patient" />
          <target value="Person" />
          <target value="RelatedPerson" />
        </SearchParameter>
      </resource>
    </entry>
    <entry>
      <fullUrl value="http://hl7.org/fhir/SearchParameter/Person-name" />
      <resource>
        <SearchParameter>
          <id value="Person-name" />
          <url value="http://hl7.org/fhir/SearchParameter/Person-name" />
          <name value="name" />
          <status value="draft" />
          <experimental value="false" />
          <publisher value="Health Level Seven International (Patient Administration)" />
          <contact>
            <telecom>
              <system value="url" />
              <value value="http://hl7.org/fhir" />
            </telecom>
          </contact>
          <contact>
            <telecom>
              <system value="url" />
              <value value="http://www.hl7.org/Special/committees/pafm/index.cfm" />
            </telecom>
          </contact>
          <code value="name" />
          <base value="Person" />
          <type value="string" />
          <description value="A server defined search that may match any of the string fields
in the HumanName, including family, give, prefix, suffix, suffix, and/or text" />
          <expression value="Person.name" />
          <xpath value="f:Person/f:name" />
          <xpathUsage value="normal" />
        </SearchParameter>
      </resource>
    </entry>
  </Bundle>
```

The definition a search operation above facilitates the definition of searchable content of a data repository.

By way of example, the processing unit 120 of the embodiment of FIG. 1 can be adapted to map each search parameter to an indexed column of the entity table. At run-time, the search parameter definition can be used to extract searchable content from repository data (when committed to the repository).

It is to be appreciated that the above exemplary definitions are provided using the known HL7 healthcare interoperability standard FHIR which facilitates domain modelling. Modern clinical data repository implementations will typically use this industry standard to define the application domain. For instance, a domain model may comprise structured definitions for up to one hundred and fifty (150) entities, and a large number of cross-references between the entities may be provided. However, the definitions may be provided in alternative forms and/or formats.

Figure 2:
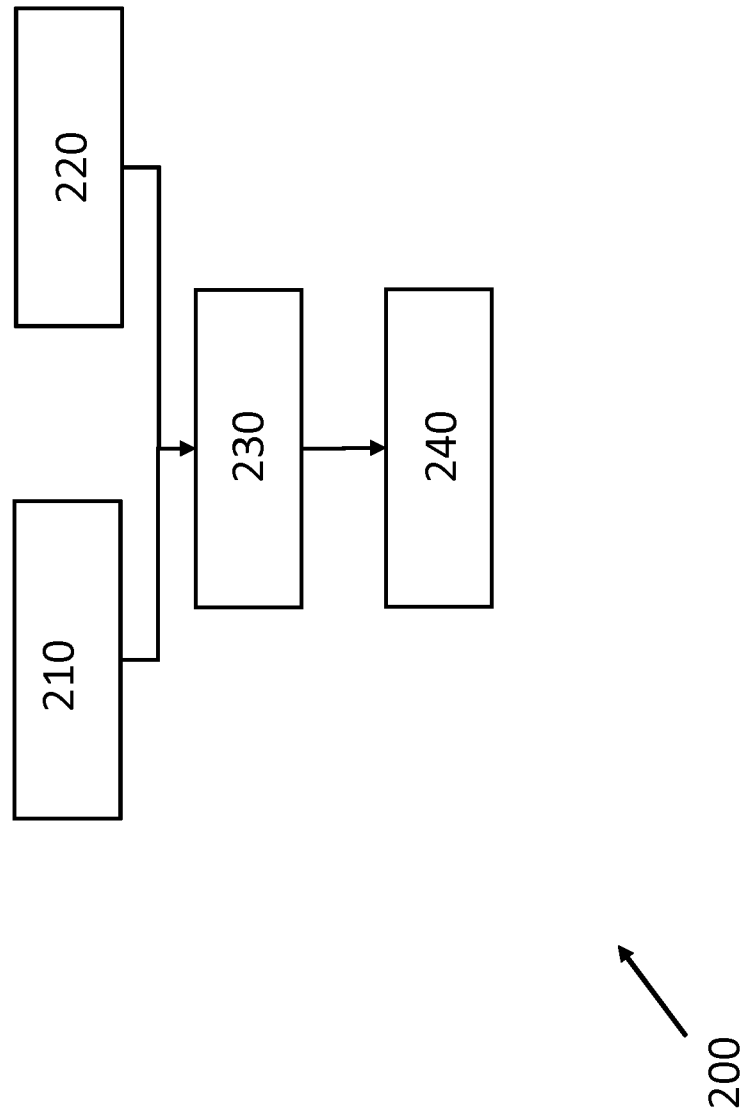
FIG. 2 is an exemplary flow diagram of a method for provisioning an instance of a data repository according to an embodiment.

Referring now to FIG. 2, there is depicted a flow diagram of a method for provisioning an instance of a data repository according to an embodiment. In step 210, an input signal representative of at least one of: an entity definition; and an operation definition is received via an input interface. Step 220 comprises a communication with one or more databases so as to obtain at least one of: an entity definition; and an operation definition. Thus, completion of steps 210 and 220 provide entity and/or operation definitions. From the obtained definitions, a domain model specification is generated in step 230 and, based on the domain model specification, an instance of a data repository is generated in step 240.

Proposed embodiments, such as that depicted in FIGS. 1 and 2 can generate a functional SQL-based repository with web API access, and this may be achieved solely based on the collection of structured definitions forming a domain model specification. Also, proposed embodiment may automatically adapt to new versions of the structured definitions.

Thus, such embodiments provide significant benefits through a reduction in the time and effort needed to implement and deploy a repository instance for a domain model. Also, time and effort associated with catering for changes in the model can also be significantly reduced by some embodiments.

Figure 3:
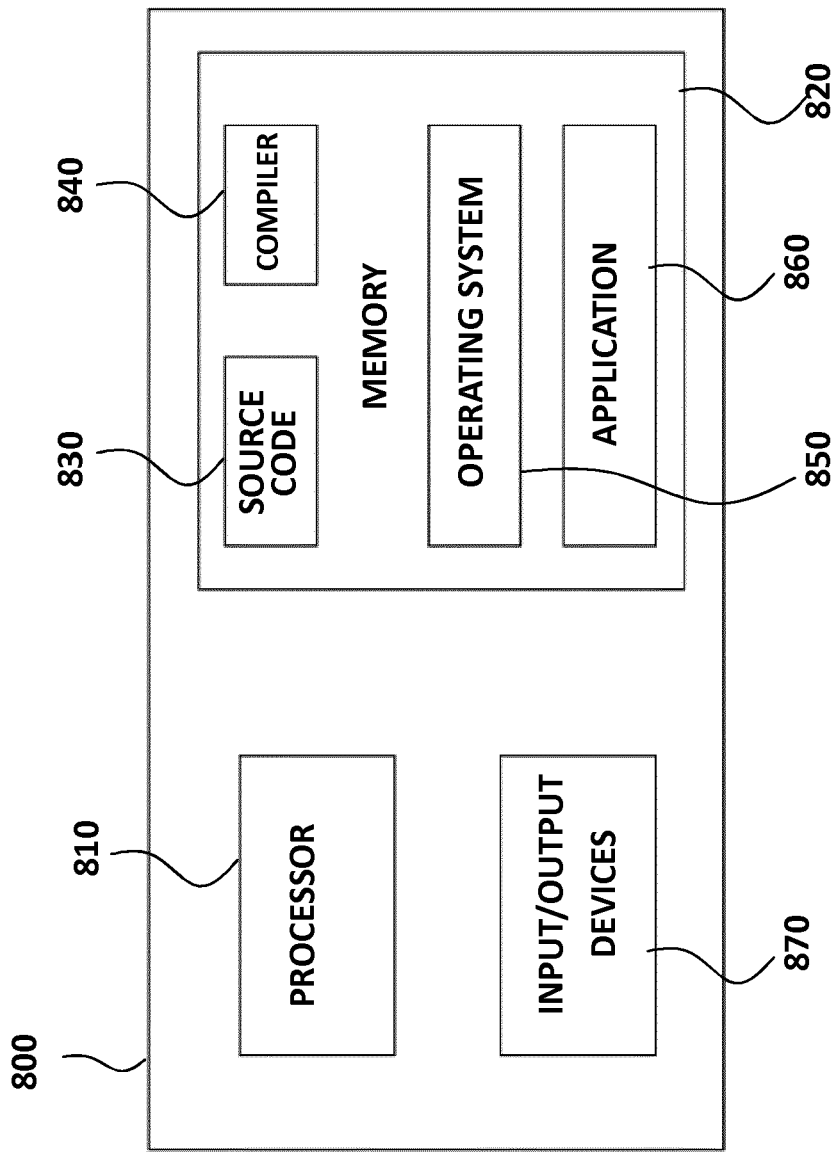
FIG. 3 is a simplified block diagram of a computer within which one or more parts of an embodiment may be employed.

FIG. 3 illustrates an example of a computer 800 within which one or more parts of an embodiment may be employed. Various operations discussed above may utilize the capabilities of the computer 800. For example, one or more parts of a system for providing patient-specific information (or display unit thereof) may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. In some embodiments, the application 860 for implementing exemplary embodiments may be applicable on commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 870 may include input devices such as, for example but not limited to, a mouse, keyboard, scanner, microphone, camera, touch-screen, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form or embodiments disclosed. Other variation to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single unit, processor or other device may fulfill the functions of several items recited in the claims. The mere fact that certain measures are recited in mutually different dependent claims does not indicate that a combination of these features cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication system. Any reference signs in the claims should not be construed as limiting the scope.

The invention claimed is:

1. An apparatus for provisioning an instance of a clinical data repository, the apparatus comprising:
    a data acquisition unit configured to obtain a domain model specification, the domain model specification comprising an entity definition defining an entity of a clinical data repository to be provisioned, and an operation definition defining searching parameters of a search operation to be supported by the clinical data repository to be provisioned, wherein the searching parameters relate to a plurality of resources so as to support a composite search query; and
    a processing unit configured to generate an instance of the clinical data repository based on the entity definition and the operation definition of the domain model specification, wherein the instance of the clinical data repository is configured to normalize clinical data relating to one or more patients according to the searching parameters and the search operation defined by the operation definition such that the instance of the clinical data repository is automatically optimized for real-time specific in-workflow analytics relative to the searching parameters and the search operation;
    wherein the data acquisition unit comprises:
        an input interface configured to receive, from a user, an input signal representative of at least one of the entity definition and the operation definition; and
        a specification unit configured to generate the domain model specification based on the input signal received from the user;
        wherein the generated instance of the clinical data repository comprises a normalized part that is optimized according to the operation definition and an entity-based part having one or more attributes defined by the entity definition to automatically optimize the search operation, and
        wherein the generated instance of the clinical data repository further comprises a service interface configured to implement the search operation defined by the operation definition.

2. The apparatus of claim 1, wherein the entity definition comprises a structured description of the entity according to a predetermined specification format.

3. The apparatus of claim 1, wherein the entity definition comprises a definition of an attribute of the entity and permissible values of the attribute.

4. The apparatus of claim 1, wherein the generated instance of the clinical data repository comprises an SQL-server instance of the data repository.

5. The apparatus of claim 1, wherein the generated instance of the clinical data repository comprises entity, junction and version tables, and searchable content and indices.

6. The apparatus of claim 1, wherein the data acquisition unit is further configured to obtain an updated version of the domain specification, and wherein the processing unit is further configured to modify the generated instance of the data repository based on the updated version of the domain model specification.

7. The apparatus of claim 1, further comprising a communication interface configured to communicate with one or more databases so as to obtain at least one of: the entity definition and the operation definition.

8. A method for provisioning an instance of a clinical data repository, the method comprising:
    receiving, from a user, an input signal via an input interface, the input signal being representative of at least one of an entity definition and an operation definition;
    generating a domain model specification based on the input signal received from the user, the domain model specification comprising an entity definition defining an entity of a clinical data repository to be provisioned, and an operation definition defining a search operation to be supported by the clinical data repository to be provisioned, wherein the search operation defines one or more searching parameters for relating to a plurality of resources so as to support a composite search query; and
    generating an instance of the clinical data repository based on the entity definition and the operation definition of the domain model specification, wherein the instance of the clinical data repository is configured to normalize clinical data relating to one or more patients according to the searching parameters and the search operation defined by the operation definition such that the instance of the clinical data repository is automatically optimized for real-time specific in-workflow analytics relative to the searching parameters and the search operation;
    wherein the generated instance of the clinical data repository comprises a normalized part that is optimized according to the operation definition and an entity-based part having one or more attributes defined by the entity definition to automatically optimize the search operation, and
    wherein the generated instance of the clinical data repository further comprises a service interface configured to implement the search operation defined by the operation definition.

9. The method of claim 8, wherein the entity definition comprises a structured description of the entity according to a predetermined specification format.

10. The method of claim 8, wherein the entity definition comprises a definition of an attribute of the entity and permissible values of the attribute.

11. The method of claim 8, wherein the generated instance of the clinical data repository comprises an SQL-server instance of the data repository.

12. The method of claim 8, wherein the generated instance of the clinical data repository comprises entity, junction and version tables, and searchable content and indices.

13. The method of claim 8, further comprising:
obtaining an updated version of the domain model specification, and
modifying the generated instance of the clinical data repository based on the updated version of the domain model specification.

14. A non-transitory computer readable medium storing instructions for provisioning an instance of a clinical data repository that, when executed by at least one processor, cause the at least one processor to:
receive, from a user, an input signal via an input interface, the input signal being representative of at least one of an entity definition and an operation definition;
generate a domain model specification based on the input signal received from the user, the domain model specification comprising an entity definition defining an entity of a clinical data repository to be provisioned, and an operation definition defining a search operation to be supported by the clinical data repository to be provisioned, wherein the search operation defines one or more searching parameters for relating to a plurality of resources so as to support a composite search query; and
generate an instance of the clinical data repository based on the entity definition and the operation definition of the domain model specification, wherein the instance of the clinical data repository is configured to normalize clinical data relating to one or more patients according to the searching parameters and the search operation defined by the operation definition such that the instance of the clinical data repository is automatically optimized for real-time specific in-workflow analytics relative to the searching parameters and the search operation;
wherein the generated instance of the clinical data repository comprises a normalized part that is optimized according to the operation definition and an entity-based part having one or more attributes defined by the entity definition to automatically optimize the search operation, and wherein the generated instance of the clinical data repository further comprises a service interface configured to implement the search operation defined by the operation definition.

15. The non-transitory computer readable medium of claim 14, wherein the generated instance of the data repository data comprises an SQL-server instance of the repository.

* * * * *